United States Patent [19]

Diana

[11] Patent Number: 4,767,788

[45] Date of Patent: Aug. 30, 1988

[54] GLUTARIC ACID VIRUCIDAL PROCESSES AND COMPOSITIONS

[75] Inventor: Guy D. Diana, Stephentown, N.Y.

[73] Assignee: Sterling Drug Inc., New York, N.Y.

[21] Appl. No.: 362,633

[22] Filed: Mar. 29, 1982

Related U.S. Application Data

[63] Continuation-in-part of Ser. No. 185,149, Sep. 8, 1980, abandoned, which is a continuation-in-part of Ser. No. 933,602, Aug. 14, 1978, abandoned.

[51] Int. Cl.$^4$ .............................................. A61K 31/19
[52] U.S. Cl. ................................... 514/574; 424/443; 424/446
[58] Field of Search ...................... 424/317, 443, 446; 514/574

[56] References Cited

PUBLICATIONS

Chemical Abstracts—44:9070(g) to 44:9071(b), 1950.
Stock et al., Cancer Research, vol. 20, No. 5, Part 2, Jun. 1960, pp. 193–195 and 236, (No. 19457).
Reed et al., J. of Infectious Diseases, vol. 133, Jun., 1976, pp. 128–135.
Hendley et al., The New England Journal of Medicine, vol. 288, pp. 1361–1364, 1973.
Gwaltney et al., Annals of Internal Medicine, vol. 88, pp. 463–467, 1978.
Gershon et al., Canadian Journal of Microbiology, vol. 22, pp. 1198–1201, 1976.

*Primary Examiner*—Jerome D. Goldberg
*Attorney, Agent, or Firm*—Theodore C. Miller; Paul E. Dupont

[57] ABSTRACT

The process of, and compositions, articles and packages for, inactivating or destroying viruses with glutaric acid are disclosed.

8 Claims, No Drawings

GLUTARIC ACID VIRUCIDAL PROCESSES AND COMPOSITIONS

CROSS-REFERENCE TO RELATED APPLICATIONS

This application is a continuation-in-part of my copending application Ser. No. 185,149 filed Sept. 8, 1980 and now abandoned, which in turn is a continuation-in-part of my copending application Ser. No. 933,602 filed Aug. 14, 1978 and now abandoned.

BACKGROUND OF THE INVENTION

1. Field of the Invention

The invention relates to glutaric acid virucidal processes, compositions, articles and packages.

2. Description of the Prior Art

It has been shown that colds caused by rhinoviruses can be transmitted from person to person or from person to object to person by way of the hands and that self-infection takes place by transfer of virus from the fingers to the nasal or conjunctival mucosa (Hendley et al., New England Journal of Medicine, vol. 288, pp. 1361–1364, 1973; Gwaltney et al., Annals of Internal Medicine, vol. 88, pp. 463–467, 1978). Similar transmission of other types of virus is also believed possible. To fill the resulting need for a topical virucidal substance and method of use and compositions thereof for interrupting the chain of virus transmission on nonliving surfaces and living tissues, especially on the hands, is therefore an object of invention. A further object of the invention is a method of reducing rhinovirus titers in the nasal passages of mammals infected by rhinoviruses using the topical virucidal substance. Still further objects of the invention are articles coated or impregnated with the virucidal substance to prevent viral contagion and packages for the virucidal substance, compositions and articles with instructions for virucidal use thereof.

Glutaric acid is a well-known organic compound having the structural formula

$HOOCCH_2CH_2CH_2COOH$.

Applicant is not aware of any prior art showing a pharmaceutical use of glutaric acid. Unsuccessful attempts to use glutaric acid for pharmaceutical purposes are shown by two prior art references.

Gershon et al. (Canadian Journal of Microbiology, vol. 22, no. 8, pp. 1198–1201, 1976) shows primarily that the dimethyl esters of the $\alpha,\omega$-alkanedicarboxylic acids of 2–12, 14 and 16 carbon atoms have antifungal activity and secondarily and contrastingly that the dicarboxylic acids themselves have little or none of this property. The only results reported for the dicarboxylic acids are those disclosed in the paragraph bridging pages 1199 and 1200:

The dicarboxylic acids, $HOOC(CH_2)_nCOOH$, possessed little or no antifungal activity. With one exception, the only level at which toxicity to some of the test organisms was observed was at $10^4$ $\mu g/ml$. The acids in which n=8 and 9 inhibited *T. mentagrophytes* at $10^3$ $\mu g/ml$ at pH 5.6 in the absence of beef serum.

These results show that noteworthy activity was observed only in the dicarboxylic acids wherein n is 8 or 9 and only at $10^3$ $\mu g/ml$ against one organism. No activity is reported specifically for glutaric acid wherein n is 3. In contrast the most active dimethyl ester was that wherein n is 7, which showed minimum inhibitory concentrations of $10^3$ $\mu g/ml$ against all six organisms and $10^2$ $\mu g/ml$ against one of the six organisms. Thus, the results show a diminishing trend of activity from the dimethyl esters wherein n is 7 to the dicarboxylic acids wherein n is 8 or 9 and away from glutaric acid wherein n is 3.

In a test against Sarcoma 180 tumor in mice glutaric acid was found to have no gradeable effect on the tumor (Stock et al., Cancer Research, vol. 20, pp. 193–195 and 236, 1960). The test was done by injection with a formulation of glutaric acid in a carboxymethylcellulose (0.5%)-saline vehicle.

SUMMARY OF THE INVENTION

In a process aspect the invention is the process of inactivating or destroying a susceptible virus which comprises contacting a locus of the virus with a virucidally effective amount of glutaric acid.

In a particular process aspect the invention is the process of reducing rhinovirus titer in the nasal mucosa of a mammal infected by a rhinovirus which comprises administering intranasally to the mammal a rhinovirucidally effective amount of glutaric acid.

In a composition aspect the invention is a composition for inactivating or destroying a susceptible virus on mammal skin which consists essentially of a virucidally effective concentration of glutaric acid and an aqueous surfactant-emollient mixture.

In an article of manufacture aspect the invention is a paper or cloth article coated or impregnated with a virucidally effective amount of glutaric acid alone or a composition consisting essentially of a virucidally effective amount of glutaric acid and a pharmaceutically acceptable vehicle for use in preventing transmission of susceptible viruses.

In a package aspect the invention is a package which consists of glutaric acid alone, a composition consisting essentially of a virucidally effective concentration of glutaric acid and a pharmaceutical vehicle, or a paper or cloth article coated or impregnated with a virucidally effective amount of glutaric acid alone or a composition consisting essentially of a virucidally effective amount of glutaric acid and a pharmaceutically acceptable vehicle, and a container with instructions for virucidal use of the glutaric acid, the composition or the article.

DETAILED DESCRIPTION OF THE INVENTION INCLUSIVE OF THE PREFERRED EMBODIMENTS

THE PROCESS

Virucidal means capable of inactivating or destroying a virus. A susceptible virus is any virus which is inactivated or destroyed by glutaric acid. The susceptible viruses are readily identified in tests such as those described below, wherein the amount or concentration of glutaric acid is considered virucidal if the virus titer is reduced by at least 99.9% (3 log units) on a nonliving surface or on living skin.

The process aspect of the invention can be carried out both in vitro and in vivo. In vitro means in or on nonliving things, especially on objects having hard or soft surfaces located or used where preventing viral transmission is desired, most especially on objects which are touched by human hands. Hard surfaces include those of building interiors, furniture and equipment and are illustrated below by Formica test plates. Soft surfaces include those of paper or cloth, for example, pre-moistened pads or tissues, dry facial tissues and hospital garments and bed clothing. In vivo means in or on a living person, plant or other animal, especially on mammal skin and mucous membrane, and most especially on hands, intranasally and intravaginally.

To carry out the process aspect of the invention the glutaric acid can be used alone or in the form of a composition consisting essentially of a virucidally effective concentration of glutaric acid and a pharmaceutical vehicle. A virucidal effect can be achieved whether the glutaric acid or glutaric acid composition is brought into contact with the virus or vice versa, or in more practical terms, whether the glutaric acid or glutaric acid composition is brought into contact with a known or potential locus of the virus.

Suspension Test of Glutaric Acid for Virucidal Activity Against Rhinoviruses

Twenty types of rhinovirus were propagated in a continuous line of HeLa (Ohio) cells. Viral titers of undiluted virus ranged from 3.5 to 6.5 $\log_{10}TCID_{50}$ per 0.2 ml. The following procedure was used for rhinovirus type 2 having a titer of 6.5 $\log_{10}TCID_{50}$ per 0.2 ml. (undiluted) and is illustrated of the procedure used for the other rhinovirus types.

Virus titrations were conducted in monolayers of HeLa (Ohio) cells. Two-tenths ml. of virus dilution was inoculated into quadruplicate tubes and allowed to incubate for 1 hr. at 33° C. Eight-tenths ml. of maintenance medium (M-199) supplemented with 5% fetal calf serum was added and the cultures were incubated at 33° C. Each tube was examined for viral cytopathic effect at 96 hr. and, for rhinovirus type 2, also at 72 hr. Glutaric acid was dissolved in maintenance medium (M-199) at concentrations of 0.5%, 1% and 2%. The pH was adjusted to 4.0. Two-tenths ml. of undiluted virus was mixed with 1.8 ml. of the 0.5%, 1% or 2% glutaric acid solution. The mixtures were allowed to stand for 10 min. at room temperature, then diluted and assayed. The virus titers were reduced by >99.99% at all three concentrations of glutaric acid.

The other nineteen rhinovirus types were similarly tested with the following results.

| Rhinovirus Type | Virus Titer $Log_{10}TCID_{50}/0.2$ ml | Percent Reduction |
| --- | --- | --- |
| 1A | 5.25 | >99.999 |
| 3 | 5.5 | >99.999 |
| 4 | 4.5 | >99.99 |
| 5 | 5.25 | >99.999 |
| 13 | 6.25 | >99.999 |
| 14 | 6.25 | >99.999 |
| 16 | 4.5 | >99.99 |
| 21 | 4.5 | >99.99 |
| 22 | 5.5 | >99.999 |
| 25 | 4.5 | >99.99 |
| 33 | 4.5 | >99.99 |
| 39 | 6.0 | >99.99 |
| 41 | 6.0 | >99.99 |
| 44 | 4.5 | >99.99 |
| 50 | 6.25 | >99.99 |
| 61 | 4.5 | >99.99 |
| 67 | 3.5 | >99.99 |
| 75 | 4.0 | 99.99 |
| 86 | 5.5 | >99.999 |

Rabbit Skin Test for Residual Virucidal Activity Against Rhinovirus Type 2

The dorsal skin of 2-3 kg. albino rabbits of either sex was used. Hair was removed by clipping and the skin was cleansed with warm water. Two circular areas, each 3 cm. in diameter, were drawn on either side of the midline of the back with indelible ink. The entire dorsal area was then scrubbed with 70% ethyl alcohol and allowed to dry overnight. On the following morning, 0.2 ml. of a 0.5%, 1%, 2% or 4% solution of glutaric acid in ethyl alcohol was applied to the circled area of the skin and distributed uniformly over the area with a sterile glass spatula. After a time interval (30 min., 1 hr., 2 hr., 4 hr. or 6 hr.), 0.1 ml. of undiluted rhinovirus type 2 was added to each test area and spread evenly over the area with a sterile glass spatula. The virus was allowed to remain on the treated skin for 10 min. Virus was recovered from the skin by firmly holding a sterile glass cylinder 3 cm. in diameter over the area and adding 5 ml. of maintenance medium (M-199) to the interior of the cylinder. The skin was rinsed by drawing the fluid into a pipette and expelling it vigorously over the area five times. The fluid was transferred to a sterile tube or viral assay. As a control for nonspecific inactivation and efficiency of virus recovery, nontreated skin was similarly inoculated with virus and the virus was recovered after contact of 10 min. To determine if the virus sampling ahd rinsing procedure resulted in a carryover of the virucidal test material into the assay system, rabbit skin was treated with an ethyl alcoholic glutaric acid solution but not inoculated with virus and after 30 min. rinsed as described above. The rinse fluids were assayed in tissue culture system and microscopically examined for cytotoxicity. As shown by the following table the 0.5% glutaric acid concentration did not have a residual virucidal effect, the 1% glutaric acid concentration had a residual virucidal effect of at least 99.9% up to four hours post-application and the 2% and 4% glutaric acid concentrations had residual virucidal effects of 99.99% up to six hours post-application in this test.

| % Glutaric Acid Concentration | % Reduction of Virus Titer Residual Virucidal Effect After | | | | |
| --- | --- | --- | --- | --- | --- |
|  | 30 min. | 1 hr. | 2 hr. | 4 hr. | 6 hr. |
| 0.5 | 0 | 0 | 0 | 0 | 0 |
| 1 | >99.9 | 99.99 | 99.9 | 99.9 | |
| 2 | >99.9 | 99.99 | 99.99 | 99.99 | 99.99 |
| 4 | | 99.99 | 99.99 | 99.99 | 99.99 |

Hard Surface Test for Residual Virucidal Activity Against Rhinovirus Type 2

Three-inch by five-inch Formica plates were cleansed by washing with Ivory soap and water, rinsing thoroughly under running tap water, then rinsing with 70% ethyl alcohol for 10 min., finally rinsing with sterile distilled water and draining and drying with Formica side down overnight. Two-tenths ml. of a 0.5%, 1% or 2% ethyl alcoholic solution of glutaric acid was evenly distributed over a circular area 5 cm. in diameter and left to dry. After a time (30 min., 1 hr., 2 hr., 4 hr. or 6 hr.), 0.1 ml. of undiluted rhinovirus type 2 was applied to the test area and spread evenly over the surface with a sterile glass spatula. The virus was allowed to remain on the treated surface for 10 min., then washed into a sterile petri dish with 5 ml. of maintenance medium (M-199). The wash fluid was recovered with a sterile pipette and expelled over the treated surface four more times, then titrated for viral content. As shown by the following table the 0.5% glutaric acid concentration had a residual virucidal effect of greater than 99.99% up to four hours post-application and the 1% and 2% glutaric acid concentrations had residual virucidal effects of 99.99% up to six hours post-application in this test.

| % Glutaric Acid Concentration | % Reduction of Virus Titer Residual Virucidal Effect After | | | | |
|---|---|---|---|---|---|
| | 30 min. | 1 hr. | 2 hr. | 4 hr. | 6 hr. |
| 0.5 | >99.99 | >99.99 | >99.99 | >99.99 | |
| 1 | 99.99 | 99.99 | 99.999 | 99.999 | 99.999 |
| 2 | 99.99 | 99.99 | 99.999 | 99.999 | 99.999 |

Hard Surface Test for Virucidal Activity Against Other Rhinovirus Types

Four-inch by six-inch Formica plates were washed and rinsed in sterile distilled water and air-dried. The plates were contaiminated by spreading 0.1 ml. of undiluted rhinovirus type 5, 13, 14, 22, 39, 41 or 50 over a two-inch square area with a sterile microscope slide and left to dry. Ten minutes later 0.2 ml. of a 0.5%, 1% or 2% solution of glutaric acid in maintenance medium (M-199) was applied evenly to the contaminated area. The virus and glutaric acid were left in contact for 10 min., then washed into a sterile petri dish with 5 ml. of maintenance medium (M-199). The wash fluid was recovered from the petri dish with a sterile pipette and the washing repeated four more times. The washings were titrated for viral content and/or cytotoxicity. Titers of all seven rhinovirus types were reduced by >99.99% by the 2% and 1% concentrations of glutaric acid. Titers of the seven rhinovirus types were reduced by the 0.5% concentration of glutaric acid as follows:

| Rhinovirus Type | % of Reduction of Virus Titer |
|---|---|
| 5 | >99.0 |
| 13 | >99.9 |
| 14 | >99.9 |
| 22 | >99.9 |
| 39 | 90 |
| 41 | >99.99 |
| 50 | >99.99 |

Tests of Glutaric Acid for Virucidal Activity Against Influenza Viruses

In these tests influenza virus A2/Japan/170/62 (6th egg passage in allantoic fluid, $EID_{50}log_{10}7.5$), influenza virus A°/PR8/34 (6th egg passage in allantoic fluid, $EID_{50}log_{10} \geq 9.0$), and ten-day old embryonated chicken (White Leghorn) eggs were used.

Five-tenths ml. of undiluted virus was mixed with 4.5 ml. of a 1%, 2% or 4% solution of glutaric acid and phosphate buffered saline. The mixture was allowed to stand at ambient temperature for 10 min. and was then rapidly diluted by ten-fold steps in phosphate-buffered saline to a final dilution of $10^{-7.0}$. To test cytotoxicity the 1%, 2% and 4% solutions of glutaric acid were diluted 9:1 with sterile phosphate-buffered saline, allowed to stand 10 min. at ambient temperature, and diluted by ten-fold steps in phosphate-buffered saline to a final dilution of $10^{-7.0}$.

Two-tenths ml. of each dilution was inoculated into the allantoic sac of each of five eggs. The eggs were incubated at 36.5° C. for 40 hr., then chilled overnight at 4° C. One-half ml. of allantoic fluid was removed from each egg and mixed with 0.5 ml. of phosphate-buffered saline in tubes. One ml. of 0.75% washed chicken red blood cells was added to each tube. The tubes were shaken and allowed to stand at ambient temperature for 40 min. Hemagglutination patterns were read and the 50% egg infectious dose ($EID_{50}$) was calculated for each concentration of glutaric acid by the method of Reed and Muench (American Journal of Hygiene. vol. 27, pp. 493–497, 1938). Cytotoxicity of glutaric acid was evaluated by examining eggs for effect on the chick embryo viability.

All three concentrations of glutaric acid reduced virus titers by >99.99%. The titers of both viruses were reduced to non-detectable levels. None of the three concentrations of glutaric acid was found to be cytotoxic.

Tests of Glutaric Acid for Virucidal Activity Against Other Viruses

In tests similar to the hard surface test against rhinoviruses types 5, 13, 14, 22, 39, 41 and 50 described above, glutaric acid was tested against eight other viruses as follows:

| Virus | $Log_{10}TCID_{50}$ per 0.2 ml. of Virus |
|---|---|
| Parainfluenza Type 3 (Soret) HA-1 Strain C-24 | 7.3 |
| Respiratory Syncytial Log Strain | 5.2 |
| Poliovirus Type III Leon (Led.) MK10+ | 7.5 |
| Poliovirus Type II YSK (Led.) MK7+ LLCL | 7.5 |
| ECHO 9 (No. 5591) | 7.0 |
| ECHO 11 (No. 5593) | 7.0 |
| Herpes Simplex Type I (Sheely) | 6.5 |
| Herpes Simplex Type 2 (Curtis) | 6.5 |

The parainfluenza virus and polioviruses were maintained in a continuous line of HeLa (Ohio) cells. The respiratory syncytial virus, ECHO viruses and herpes simplex viruses were maintained in a continuous line of BSC-1 (monkey kidney) cells.

The results of the tests showed that the minumum concentration of glutaric acid necessary to reduce the titers of the herpes simplex viruses types 1 and 2 and respiratory syncytial virus by >99.99% was 1%, that the minimum concentration of glutaric acid necessary to reduce the titer of parainfluenza virus type 3 by 99.99% was 2%, and that the minimum concentration of glutaric acid necessary to reduce the titers of influenza viruses $A_2$(Japan 170) and $A_o$(PR8) by >99.99% was 1%. The results also showed that a 4% concentration of glutaric acid was not virucidal against polioviruses types II and III and ECHO viruses types 9 and 11.

Test of Activity of Glutaric Acid Intranasally Against Rhinovirus Infection in Hamsters Equine rhinovirus prepared in Vero cells and instilled into the nostrils of hamsters was found to grow in their nasal passages for at least 7 days. Washing of the nasal passages on days 3, 4 and 7 of this period showed appreciable virus titers on days 3 and 4 and lower titers on day 7. Virus titers in nasal washes on days 3 and 4 post-infection were similar to those reported in human rhinovirus infections and ranged from 2.0 to 3.0 $\log_{10}$ $TCID_{50}$ per 0.2 ml. Because of the similarity of the upper respiratory infection in hamsters produced by equine rhinovirus and the upper respiratory infection in humans produced by human rhinovirus and because of the lack of an appropriate laboratory animal in which human rhinovirus is able to grow, the hamster infection was used as a model of the human infection to study the effect of intranasally applied glutaric acid on the growth of the rhinovirus.

Syrian hamsters of either sex each weighing about 100 grams were housed in individual cages for the test. A group of six hamsters was used at each medication level. Equine rhinovirus was grown in tissue cultures of Vero cells and stored in heat-sealed glass ampules at $-90°$ C. Infection was accomplished by instilling 0.05 ml. of undiluted virus into each hamster nostril while the hamster was under light barbiturate anesthesia.

The following virus recovery and assay procedure was used. Each hamster nostril was washed with 1.5 ml. of medium M-199 containing penicillin (1000 units/ml.) and streptomyin (1000 mcg./ml.). The washings from each hamster were combined, separated into two aliquots and stored at $-90°$ C. until assayed. To carry out the assay an aliquot was thawed and diluted from $10^{-1}$ to $10^{-3}$ in Eagle's medium plus 2% newborn calf serum. Monolayers of Vero cells grown in cluster dishes (six wells per dish) were prepared by removing the growth medium. One ml. of each virus dilution was then added to each of three wells. The virus was removed from the cell monolayers after one hour at 37° C. in a 5% $CO_2$ atmosphere. To each well was added 3.0 ml. of equal parts of 2X medium M-199 and 1.5% agar. Each dish was then incubated for four days at 37° C. in a 5% $CO_2$ atmosphere. Formalin (1%)-sodium-acetate (2%) (1 ml.) then added to each well, and the dish was stored for 24 hours at 4° C. The agar was then gently removed, the cell monolayers were stained with crystal violet, the plaques produced by the virus were counted, and the geometric mean plaque count for each dilution was determined.

In a first test the titer of undiluted equine rhinovirus was 8.0 $\log_{10}TCID_{50}$ per 0.2 ml. Medication was administered in the form of droplets of 0.05 ml. volume in each nostril with a syringe or by a single aerosol application in each nostril four times a day for four consecutive days startin four hours postinfection on the first day. A droplet formulation of 2%, 5% or 10% glutaric acid concentration in water containing 0.45% lactic acid and adjusted to pH 3.5 with sodium hydroxide and an aerosol formulation of 2%, 5% or 10% glutaric acid concentration in water adjusted to pH 4.0 with sodium hydroxide were tested. As shown by the following summary of results the 10% and 5% droplet formulations reduced viral titers significantly by about 90% or more on the third and fourth days postinfection and the 2% droplet formulation reduced viral titers significantly by more than 90% on the fourth day postinfection but by less than 90% on the third day postinfection compared with placebo controls.

| Glutaric Acid Concentration | Droplet Formulation | |
|---|---|---|
| | $\log_{10}$ Mean Plaque Forming Units Per Milliliter | |
| | Day 3 | Day 4 |
| 10% | 1.17 | 0.73 |
| 5% | 0.74 | 0.39 |
| 2% | 1.60 | 1.22 |
| Placebo | 2.07 | 2.44 |
| No Medication | 3.13 | 3.11 |

As shown by the following summary of results, whereas the 2% aerosol formulation did not significantly reduce viral titers. the 10% and 5% aerosol formulations reduced viral titers by more than 90% on the third, fourth and seventh days post-infection compared with placebo controls.

| Glutaric Acid Concentration | Aerosol Formulation | | |
|---|---|---|---|
| | $\log_{10}$ Mean Plaque Forming Units Per Milliliter | | |
| | Day 3 | Day 4 | Day 7 |
| 10% | 0.25 | .0 | 0 |
| 5% | 0.36 | 0 | 0 |
| 2% | 2.06 | 1.81 | 1.17 |
| Placebo | 1.53 | 1.52 | 0.75 |
| No Medication | 2.5 | 2.16 | 0.91 |

In a second test the titer of undiluted equine rhinovirus was 5.7 $\log_{10}TCID_{50}$ per 0.2 ml. Medication was administered in the form of a nasal spray from plastic squeeze bottles equipped with teflon adapters to fit the external nasal passages of the hamsters. On the first day two doses were administered four hours apart starting four hours postinfection. On each of the next four days four doses were administered. Formulations of 2%, 5% and 10% glutaric acid concentrations in water adjusted to pH 4.0 with sodium hydroxide were again tested. As shown by the following summary of results all three concentrations of glutaric acid reduced viral titers significantly by more than 90% on the third and fourth days postinfection and to undetectable levels on the seventh day postinfection.

| Glutaric Acid Concentration | Spray Formulation | | |
|---|---|---|---|
| | $\log_{10}$ Mean Plaque Forming Units Per Milliliter | | |
| | Day 3 | Day 4 | Day 7 |
| 10% | 0.57 | 0.27 | 0 |
| 5% | 0 | 0.42 | 0 |
| 2% | 0.37 | 0 | 0 |
| Placebo | 2.05 | 1.3 | 0.76 |
| No Medication | 2.2 | 2.6 | 2.35 |

Test of Activity of Glutaric Acid Against Herpesvirus Hominis Type 2 in Mouse Genital Infection Intravaginal administration of aqueous solutions of glutaric acid at concentrations of 1, 2, 4, 8 and 10% to mice infected by the intravaginal route with herpesvirus hominis type 2 resulted in increased survival rate of the mice compared with placebo-treated controls as shown by the following table.

| Glutaric Acid Concentration (%) | Survival Rate (%) |
|---|---|
| Placebo | 10 |
| 1 | 30 |
| 2 | 60 |
| 4 | 50 |
| 8 | 60 |
| 10 | 70 |

THE COMPOSITIONS

The compositions of the invention are intended for topical virucidal use both in vitro and in vivo, especially on mammal skin and most especially on human hands. For these purposes the glutaric acid can be formulated in any appropriate vehicle, provided that the glutaric acid and the vehicle are compatible, that is, that the virucidal activity of the glutaric acid is not diminished by the vehicle. Thus, the compositions can be in the form of creams, foams, lotions, ointments, solutions or sprays. The vehicle diluent can be aqueous or non-aqueous, for example alcoholic or oleaginous, or a mixture thereof, and may additionallY contain surfactants, emollients, lubricants, stabilizers, dyes, perfumes, antimicrobial agents either as active ingredients or as preservatives and acid or base for adjustment of pH. The preferred pH is about 4. Conventional methods are used in preparing the compositions.

The foregoing compositions can be dispensed in premoistened pads or tissues. The latter can be packaged individually as described, for example, in U.S. Pat. No. 3,057,467 or multiply, in separate sheets as described, for example, in U.S. Pat. No. 3,836,044 or in a roll as described, for example, in U.S. Pat. No. 4,017,002.

EXAMPLE 1

The following example is a composition intended for use as a virucidal hand lotion wherein the vehicle is an aqueous surfactant-emollient mixture.

| Ingredient | Percent by Weight |
|---|---|
| Glutaric Acid | 1.00xxx |
| Glyceryl Stearate (and) PEG-100 Stearate | 3.00xxx |
| PPG-12-Buteth-16 | 2.00xxx |
| Cetyl Alcohol | 1.50xxx |
| Myristyl Alcohol | 1.50xxx |
| PEG-4 Laurate | 1.00xxx |
| PEG-4 Stearate | 0.500xx |
| Glycerin | 0.500xx |
| Perfume | 0.300xx |
| Carbomer-934P | 0.200xx |
| Zinc Pyrithione | 0.00200 |
| Dye | 0.100xx |
| Water to make | 100.00xxx |

EXAMPLE 2

The composition corresponding to the composition of Example 1 except that 2.00% glutaric acid was substituted for 1.00% glutaric acid was also prepared.

EXAMPLE 3

The following example is a composition intended for use as a virucidal foam wherein the vehicle is an aqueous ethyl alcoholic surfactant-emollient aerosol mixture.

| Ingredient | Percent by Weight |
|---|---|
| Glutaric Acid | 1.00xx |
| Steareth-2 | 1.50xx |
| Laneth-16 | 1.00xx |
| Cetyl Alcohol | 0.800x |
| Myristyl Alcohol | 0.200x |
| Perfume | 0.0500 |
| Alcohol, USP | 45.2xxx |
| Purified Water | 36.3xxx |
| Propane | 0.800x |
| Isobutane | 4.20xx |
| Water to Make | 100.0xxx |

EXAMPLE 4

A composition corresponding to the composition of Example 3 except that 2.00% glutaric acid was substituted for 1.00% glutaric acid was also prepared.

Test of the Compositions of Example 1-4 in the Rabbit Skin Test for Residual Virucidal Activity Against Rhinovirus Type 2

The compositions of the foregoing examples were tested in the rabbit skin test described above except that 0.4 ml. of the compositions of Example 1 and 2 and a three-fourths inch ball of foam of the compositions of Examples 3 and 4 were used and the compositions and virus were spread on the test site with a gloved finger instead of a sterile glass spatula. The following results were obtained.

| Example | % Reduction of Virus Titer | | | | |
|---|---|---|---|---|---|
| | 30 min | 1 hr | 2 hr | 4 hr | 6 hr |
| 1 | 99.9 | 99.9 | 99.9 | 99.9 | |
| | 99.9 | 99.9 | 99.9 | 99.9 | 99.9 |
| 2 | >99.9 | >99.9 | >99.9 | >99.9 | |
| | >99.9 | >99.9 | >99.9 | >99.9 | >99.9 |
| 3 | >99.9 | >99.9 | >99.9 | >99.9 | >99.9 |
| | >99.9 | >99.9 | >99.9 | >99.9 | >99.9 |
| 4 | >99.9 | >99.9 | >99.9 | >99.9 | >99.9 |

EXAMPLE 5

The following example is a composition intended for use as a virucidal hand lotion wherein the vehicle is an aqueous surfactant-emollient mixture and wherein sodium benzoate is added as an antimicrobial agent.

| Ingredient | Percent by Weight |
|---|---|
| Glutaric Acid | 2.00xx |
| Sodium Benzoate | 0.500x |
| PPG-12-Buteth-16 | 3.50xx |
| Glyceryl Stearate (and) PEG-100 Stearate | 3.00xx |
| Myristyl Alcohol | 1.50xx |
| Cetyl Alcohol | 1.10xx |
| PEG-4 Laurate | 1.00xx |
| PEG-4 Stearate | 0.500x |
| Glycerin | 0.500x |
| Titanium Dioxide | 0.250x |
| Carbomer 934P | 0.200x |
| Perfume | 0.0375 |
| Sodium Hydroxide to adjust pH to 4.0 | |
| Water to make | 100.00xx |

Hand lotions according to and corresponding to Example 5 and containing 0.5%, 1% and 2% glutaric acid with or without 0.5% sodium benzoate were compared for residual virucidal activity against rhinovirus type 2 and bactericidal activity against *Serratia marcescens* on rabbit skin. The greatest virucidal activity was achieved with 1% or 2% glutaric acid with or without sodium benzoate after the virus was placed on rabbit skin which had been treated six hours earlier with the lotions. The lotion containing 0.5% glutaric acid and 0.5% sodium benzoate was active to a lesser degree while the two placebos, one containing neither agent and and the other containing only 0.5% sodium benzoate, had no virucidal activity. The lotion containing 2% glutaric acid and 0.5% sodium benzoate had the greatest bactericidal activity. In two separate experiments, a reduction of 5.0 logs of the bacterial titer was achieved on rabbit skin treated 2 hrs. earlier. The lotion containing 1% glutaric acid and 0.5% sodium benzoate produced a minimal reduction of bacterial titer (>1.0 log) and one containing 2% glutaric acid alone achieved a significant reduction of 5.0 logs. Thus, it appears that the glutaric acid plays a role not only as a virucidal but also as a bactericidal agent against *Serratia marcescens*.

Hand lotions corresponding to Example 5 and containing 0.5% dehydroacetic acid, 0.17% hexylresorcinol or 0.5% phenoxyethanol instead of 0.5% sodium benzoate were also shown to be virucidal against rhinovirus type 2 and bactericidal against *Serratia marcescens* in similar tests.

THE ARTICLES

The article of manufacture aspect of the invention is described in part above with the process aspect of the invention and the definitions of in vitro and objects having soft surfaces and the composition aspect of the invention and the dispensing of the compositions in pre-moistened pads or tissues.

The paper or cloth articles of the invention are coated or impregnated with glutaric acid or a glutaric acid composition by dipping, spreading, spraying, dusting or condensing glutaric acid vapor and are otherwise made by known methods of manufacture.

Dry facial tissues containing glutaric acid at concentrations of 0.5, 1.0 and 2.0 mg. per square inch, which were prepared by spraying aqueous solutions of glutaric acid onto commercially available paper tissues and drying them, inactivated rhinovirus type 2 by greater than 99.99% after a 10 min. contact at room temperature.

THE PACKAGES

The package aspect of the invention combines the other aspects of the invention and is the form in which the invention is contemplated to be sold. The container can be of any type for solid or liquid contents. The instructions for virucidal use of the process, composition or article aspect of the invention can be a label, package insert or any other means of communicating such use.

I claim:

1. The process of inactivating or destroying a susceptible virus which comprises contacting the virus or a locus of the virus with a virucidally effective amount of glutaric acid.

2. The process according to claim 1 wherein the virus is a rhinovirus, a herpes simplex virus, an influenza virus, a parainfluenza virus or a respiratory syncytial virus.

3. The process according to claim 1 wherein the glutaric acid is in the form of a composition consisting essentially of a virucidally effective concentration of glutaric acid and a pharmaceutical vehicle.

4. The process of reducing rhinovirus titer in the nasal mucosa of a mammal infected by a rhinovirus which comprises administering intranasally to the mammal a rhinovirucidally effective amount of glutaric acid.

5. The process according to claim 4 wherein the glutaric acid is in the form of a composition consisting essentially of a virucidally effective concentration of glutaric acid and a pharmaceutical vehicle.

6. A composition for inactivating or destroying a susceptible virus on mammal skin which consists essentially of a virucidally effective concentration of glutaric acid and an aqueous surfactant-emollient mixture.

7. A composition according to claim 6 wherein the aqueous surfactant-emollient mixture is an aerosol mixture.

8. A composition according to claim 6 prepared for being dispensed in pre-moistened pads or tissues.

* * * * *